US010751351B2

(12) United States Patent
Vuagniaux et al.

(10) Patent No.: US 10,751,351 B2
(45) Date of Patent: Aug. 25, 2020

(54) MEDICAMENT FOR TREATMENT OF DIABETIC FOOT INFECTIONS

(71) Applicant: Debiopharm International S.A., Lausanne (CH)

(72) Inventors: Grégoire Vuagniaux, Lausanne (CH); Linda Kadi, Segny (FR); Frederick Wittke, Zollikofen (CH)

(73) Assignee: Debiopharm International S.A., Lausanne (CH)

( * ) Notice: Subject to any disclaimer, the term of this patent is extended or adjusted under 35 U.S.C. 154(b) by 0 days.

(21) Appl. No.: 16/079,804

(22) PCT Filed: Feb. 27, 2017

(86) PCT No.: PCT/EP2017/054470
§ 371 (c)(1),
(2) Date: Aug. 24, 2018

(87) PCT Pub. No.: WO2017/144717
PCT Pub. Date: Aug. 31, 2017

(65) Prior Publication Data
US 2019/0054100 A1   Feb. 21, 2019

(30) Foreign Application Priority Data

Feb. 26, 2016 (EP) .................................. 16157685
Feb. 26, 2016 (EP) .................................. 16157688

(51) Int. Cl.
*A61K 31/675* (2006.01)
*A61K 31/4375* (2006.01)
*A61P 31/04* (2006.01)
*A61K 9/00* (2006.01)

(52) U.S. Cl.
CPC .......... *A61K 31/675* (2013.01); *A61K 9/0019* (2013.01); *A61K 9/0053* (2013.01); *A61K 31/4375* (2013.01); *A61P 31/04* (2018.01)

(58) Field of Classification Search
CPC .................................................. A61K 31/675
See application file for complete search history.

(56) References Cited

U.S. PATENT DOCUMENTS

| | | |
|---|---|---|
| 3,828,068 A | 8/1974 | Minieri |
| 4,154,943 A | 5/1979 | Kuehne |
| 4,977,159 A | 12/1990 | Sevrin et al. |
| 5,416,193 A | 5/1995 | Desai |
| 5,614,551 A | 3/1997 | Dick et al. |
| 5,624,941 A | 4/1997 | Barth et al. |
| 5,932,743 A | 8/1999 | Collini et al. |
| 5,985,867 A | 11/1999 | Rodgers et al. |
| 5,989,832 A | 11/1999 | Trias et al. |
| 6,133,260 A | 10/2000 | Matzke et al. |
| 6,174,878 B1 | 1/2001 | Gamache et al. |
| 6,184,380 B1 | 2/2001 | Chiu et al. |
| 6,187,341 B1 | 2/2001 | Johnson et al. |
| 6,194,429 B1 | 2/2001 | Guinn et al. |
| 6,194,441 B1 | 2/2001 | Roberts et al. |
| 6,198,000 B1 | 3/2001 | Hawkins |
| 6,221,859 B1 | 4/2001 | Dorso et al. |
| 6,221,864 B1 | 4/2001 | Hirayama et al. |
| 6,235,908 B1 | 5/2001 | Fey |
| 6,239,113 B1 | 5/2001 | Dawson et al. |
| 6,239,141 B1 | 5/2001 | Allen et al. |
| 6,248,363 B1 | 6/2001 | Patel et al. |
| 6,267,985 B1 | 7/2001 | Chen et al. |
| 6,277,836 B1 | 8/2001 | Borody |
| 6,288,239 B1 | 9/2001 | Hollingsworth |
| 6,291,462 B1 | 9/2001 | Bartholomaeus et al. |
| 6,294,192 B1 | 9/2001 | Patel et al. |
| 6,303,572 B1 | 10/2001 | Rowe |
| 6,309,663 B1 | 10/2001 | Patel et al. |
| 6,333,045 B1 | 12/2001 | Yasueda et al. |
| 6,340,689 B1 | 1/2002 | Dubois et al. |
| 6,346,391 B1 | 2/2002 | Oethinger et al. |
| 6,367,985 B1 | 4/2002 | Lee et al. |
| 6,372,752 B1 | 4/2002 | Staveski et al. |
| 6,388,070 B1 | 5/2002 | Deshpande et al. |
| 6,395,746 B1 | 5/2002 | Cagle et al. |
| 6,399,629 B1 | 6/2002 | Chamberland et al. |
| 6,406,880 B1 | 6/2002 | Thornton |
| 6,423,341 B1 | 7/2002 | Yamaguchi |

(Continued)

FOREIGN PATENT DOCUMENTS

| | | |
|---|---|---|
| CA | 2444597 A1 | 10/2002 |
| CA | 2568914 A1 | 12/2005 |

(Continued)

OTHER PUBLICATIONS

Boffeli et al. J. Foot Ankle Surg, 2014, 53(6):720-6.*
Hill et al., Am J. Surg, 1999, 177(4): 282-6.*
International Preliminary Report on Patentability dated Jan. 20, 2009 in connection with PCT/CA2007/001277.
International Search Report and Written Opinion dated May 26, 2017 in connection with PCT/EP2017/054470.
International Search Report and Written Opinion dated Dec. 3, 2013 in connection with PCT/IB2013/001780.
International Search Report and Written Opinion dated Nov. 30, 2011 in connection with PCT/US2011/040187.
International Search Report dated Jun. 5, 2008 in connection with PCT/CA2008/000300.
International Search Report dated Sep. 12, 2007 in connection with PCT/US2006/045903.

(Continued)

*Primary Examiner* — Rei Tsang Shiao
(74) *Attorney, Agent, or Firm* — Wolf, Greenfield & Sacks, P.C.

(57) ABSTRACT

The present invention provides means and methods for treating diabetic foot infections. In particular, drug compounds are provided that combine a high therapeutic activity against *Staphylococcus* Spp. bacteria with a high degree of bone penetration and vasodilatory effects. This unique combination of properties allows to accomplish high local concentrations of the drug at the site of infection even in diabetic foot patients typically having poor blood perfusion at the site of infection.

24 Claims, No Drawings

(56) References Cited

U.S. PATENT DOCUMENTS

| | | |
|---|---|---|
| 6,423,741 B1 | 7/2002 | Khanuja et al. |
| 6,428,579 B1 | 8/2002 | Valentini |
| 6,432,444 B1 | 8/2002 | Fischetti et al. |
| 6,432,670 B1 | 8/2002 | Payne et al. |
| 6,436,980 B1 | 8/2002 | Leger et al. |
| 6,441,162 B2 | 8/2002 | Yasui et al. |
| 6,448,054 B1 | 9/2002 | Poznansky et al. |
| 6,448,238 B1 | 9/2002 | Shoichet et al. |
| 6,448,449 B2 | 9/2002 | Larrow |
| 6,451,339 B2 | 9/2002 | Patel et al. |
| 6,451,816 B1 | 9/2002 | Biedermann et al. |
| 6,461,607 B1 | 10/2002 | Farmer |
| 6,461,829 B1 | 10/2002 | Kahne |
| 6,465,429 B1 | 10/2002 | Hancock et al. |
| 6,468,964 B1 | 10/2002 | Rowe |
| 6,469,046 B1 | 10/2002 | Daines et al. |
| 6,486,148 B2 | 11/2002 | Savage et al. |
| 6,486,149 B2 | 11/2002 | Onodera et al. |
| 6,486,165 B2 | 11/2002 | Zhang et al. |
| 6,489,318 B1 | 12/2002 | Copar et al. |
| 6,492,351 B1 | 12/2002 | Zhang et al. |
| 6,495,158 B1 | 12/2002 | Buseman et al. |
| 6,495,161 B1 | 12/2002 | Soon-Shiong et al. |
| 6,495,551 B1 | 12/2002 | Betts et al. |
| 6,497,886 B1 | 12/2002 | Breitenbach et al. |
| 6,500,459 B1 | 12/2002 | Chhabra et al. |
| 6,500,463 B1 | 12/2002 | Van Lengerich |
| 6,503,539 B2 | 1/2003 | Gestrelius et al. |
| 6,503,881 B2 | 1/2003 | Krieger et al. |
| 6,503,903 B1 | 1/2003 | Miller et al. |
| 6,503,906 B1 | 1/2003 | Lee |
| 6,503,908 B1 | 1/2003 | Maw |
| 6,503,953 B2 | 1/2003 | Vyden |
| 6,503,955 B1 | 1/2003 | Dobrozsi et al. |
| 6,509,327 B1 | 1/2003 | Cagle et al. |
| 6,514,535 B2 | 2/2003 | Marchant |
| 6,514,541 B2 | 2/2003 | Khanuja et al. |
| 6,514,953 B1 | 2/2003 | Armitage et al. |
| 6,514,962 B1 | 2/2003 | Shibatani et al. |
| 6,514,986 B2 | 2/2003 | de Souza et al. |
| 6,515,113 B2 | 2/2003 | Raymond et al. |
| 6,517,827 B1 | 2/2003 | Bacon Kurtz et al. |
| 6,518,239 B1 | 2/2003 | Kuo et al. |
| 6,518,263 B1 | 2/2003 | Nishitani et al. |
| 6,518,270 B1 | 2/2003 | Amin et al. |
| 6,518,487 B1 | 2/2003 | Lowe et al. |
| 6,521,408 B1 | 2/2003 | Kawasaki |
| 6,525,066 B2 | 2/2003 | Fukumoto et al. |
| 6,527,759 B1 | 3/2003 | Tachibana et al. |
| 6,528,089 B1 | 3/2003 | Kothrade et al. |
| 6,531,126 B2 | 3/2003 | Farmer |
| 6,531,291 B1 | 3/2003 | Kabbash et al. |
| 6,531,465 B1 | 3/2003 | Ascher et al. |
| 6,531,508 B1 | 3/2003 | Nomura et al. |
| 6,531,649 B1 | 3/2003 | Mannerloef et al. |
| 6,559,172 B1 | 5/2003 | Heerding et al. |
| 6,573,272 B1 | 6/2003 | Miller et al. |
| 6,673,941 B2 | 1/2004 | Heerding et al. |
| 6,703,684 B2 | 3/2004 | Udrea et al. |
| 6,730,684 B1 | 5/2004 | Miller et al. |
| 6,762,201 B1 | 7/2004 | Miller et al. |
| 6,765,005 B2 | 7/2004 | Miller et al. |
| 6,821,746 B2 | 11/2004 | DeWolf, Jr. et al. |
| 6,846,819 B1 | 1/2005 | Miller et al. |
| 6,951,729 B1 | 10/2005 | DeWolf, Jr. et al. |
| 6,964,970 B2 | 11/2005 | Miller et al. |
| 6,995,254 B1 | 2/2006 | Payne et al. |
| 7,048,926 B2 | 5/2006 | Brandt et al. |
| 7,049,310 B2 | 5/2006 | Burgess et al. |
| 7,250,424 B2 | 7/2007 | Burgess et al. |
| 7,449,458 B2 | 11/2008 | Bhamidipati et al. |
| 7,524,843 B2 | 4/2009 | Miller et al. |
| 7,538,108 B2 | 5/2009 | Singh et al. |
| 7,557,125 B2 | 7/2009 | Miller et al. |
| 7,563,892 B1 | 7/2009 | Singh et al. |
| 7,741,339 B2 | 6/2010 | Burgess et al. |
| 7,790,709 B2 | 9/2010 | Berman et al. |
| 7,790,716 B2 | 9/2010 | Miller et al. |
| 7,879,872 B2 | 2/2011 | Berman et al. |
| 7,989,448 B2 | 8/2011 | Singh et al. |
| 8,153,652 B2 | 4/2012 | Burgess et al. |
| 8,163,902 B2 | 4/2012 | Bhamidipati et al. |
| 8,173,646 B2 | 5/2012 | Miller et al. |
| 8,211,888 B2 | 7/2012 | Singh et al. |
| 8,211,889 B2 | 7/2012 | Singh et al. |
| 8,263,613 B2 | 9/2012 | Pauls et al. |
| 8,318,720 B2 | 11/2012 | Pauls et al. |
| 8,450,307 B2 | 5/2013 | Sargent et al. |
| 8,901,105 B2 * | 12/2014 | Partridge ............ A61K 31/675 514/81 |
| 2001/0016662 A1 | 8/2001 | Golik et al. |
| 2003/0232850 A1 | 12/2003 | Miller et al. |
| 2004/0053814 A1 | 3/2004 | Brandt et al. |
| 2005/0250810 A1 | 11/2005 | Miller et al. |
| 2006/0142265 A1 | 6/2006 | Berman et al. |
| 2006/0183908 A1 | 8/2006 | Berman et al. |
| 2006/0211657 A1 | 9/2006 | Singh et al. |
| 2006/0234983 A1 | 10/2006 | Singh et al. |
| 2008/0125423 A1 | 5/2008 | Miller et al. |
| 2009/0042927 A1 | 2/2009 | Pauls et al. |
| 2009/0156578 A1 | 6/2009 | Pauls et al. |
| 2009/0221699 A1 | 9/2009 | Burgess et al. |
| 2010/0130470 A1 | 5/2010 | Pauls et al. |
| 2011/0124633 A1 | 5/2011 | Berman et al. |
| 2012/0010127 A1 | 1/2012 | Berman et al. |
| 2013/0237523 A1 | 9/2013 | Pauls et al. |
| 2013/0281442 A1 | 10/2013 | Hafkin |
| 2014/0107106 A1 | 4/2014 | Sargent et al. |

FOREIGN PATENT DOCUMENTS

| | | |
|---|---|---|
| CA | 2776849 A1 | 5/2011 |
| CN | 102675311 A | 9/2012 |
| EP | 0407200 A1 | 1/1991 |
| EP | 0953570 A1 | 11/1999 |
| EP | 1000935 A1 | 5/2000 |
| HU | 0203122 B | 5/1991 |
| HU | 2106079 B | 6/1995 |
| JP | 11-302173 A | 11/1999 |
| WO | WO 93/04035 A1 | 3/1993 |
| WO | WO 95/18619 A1 | 7/1995 |
| WO | WO 96/00730 A1 | 1/1996 |
| WO | WO 97/48696 A1 | 12/1997 |
| WO | WO 98/57952 A1 | 12/1998 |
| WO | WO 99/24406 A1 | 5/1999 |
| WO | WO 00/27628 A1 | 5/2000 |
| WO | WO 00/57933 A1 | 10/2000 |
| WO | WO 01/26652 | 4/2001 |
| WO | WO 01/26654 A1 | 4/2001 |
| WO | WO 01/27103 A1 | 4/2001 |
| WO | WO 01/41573 A1 | 6/2001 |
| WO | WO 01/48248 A2 | 7/2001 |
| WO | WO 01/70172 A2 | 9/2001 |
| WO | WO 02/10332 A1 | 2/2002 |
| WO | WO 02/42273 A2 | 5/2002 |
| WO | WO 02/48097 A1 | 6/2002 |
| WO | WO 02/064572 A1 | 8/2002 |
| WO | WO 03/086396 A1 | 10/2003 |
| WO | WO 03/088897 A2 | 10/2003 |
| WO | WO 04/014869 A2 | 2/2004 |
| WO | WO 04/52890 A1 | 6/2004 |
| WO | WO 04/82586 A2 | 9/2004 |
| WO | WO 2005/090367 A1 | 9/2005 |
| WO | WO 07/053131 A2 | 5/2007 |
| WO | WO 07/067416 A2 | 6/2007 |
| WO | WO 08/009122 A1 | 1/2008 |
| WO | WO 2008/064274 A1 | 5/2008 |
| WO | WO 08/098374 A1 | 8/2008 |
| WO | WO 2009/003136 A1 | 12/2008 |
| WO | WO 2010/151689 | 12/2010 |
| WO | WO 2010/151711 | 12/2010 |
| WO | WO 2011/002999 A1 | 1/2011 |
| WO | WO 2011/061214 A1 | 5/2011 |

(56) References Cited

FOREIGN PATENT DOCUMENTS

| | | |
|---|---|---|
| WO | WO 2011/156811 A2 | 12/2011 |
| WO | WO 2013/080222 | 6/2013 |
| WO | WO 2013/190384 A1 | 12/2013 |

OTHER PUBLICATIONS

Extended European Search Report dated Jul. 16, 2014 in connection with EP08714623.9.
European Search Report dated Oct. 30, 2013 in connection with EP11793310.1.
Hungarian Search Report dated Dec. 31, 2003 in connection with Hungarian Application No. P0203122.
Abou-Gharbia et al., Psychotropic agents: synthesis and antipsychotic activity of substituted beta-carbolines, J Med Chem. 1987;30(6):1100-5.
Ahsan et al. Reserpine Analogues: Synthesis of B-Carboline Derivatives, J. Chem. Soc. 1963;3928-30.
Annesley et al. Glucuronidation of prodrug reactive site: isolation and characterization of oxymethylglucuronide metabolite of fosphenytoin, Clin Chem, May 2001;47(5):910-8.
Arora et al., Cutaneous microcirculation in the neuropathic diabetic foot improves significantly but not completely after successful lower extremity revascularization. J Vasc Surg. Mar. 2002;35(3):501-5.
Barkema et al., Invited Review: The Role of Cow, Pathogen, and Treatment Regimen in the Therapeutic Success of Bovine *Staphylococcus aureus* Mastitis, J Dairy Science. 2006;89:1877-95.
Bastin et al., Salt Selection and Optimisation Procedure for Pharmaceutical New Chemical Entities, Organic Process Res. & Dev., 2000;4(5):427-35.
Berge et al., Pharmaceuticals Salts, J. of Pharm. Sciences, 1977;66(1):1-19.
Bergler et al., Protein EnvM is the NADH-dependent enoyl-ACP reductase (FabI) of *Escherichia coli*, J Biol Chem. Feb. 25, 1994;69(8):5493-6.
Chen et al., Synthesis and Antibacterial Evaluation of Certain Quinolone Derivatives, Journal of Medicinal Chemistry. 2001;44:2374-7.
Claus et al., Formaldehydabspaltende Phenolcarbonsaurederivte Monatsh. Chem. 1966;97:271-9.
Database CA on STN, AN 7:66733, Rosenmund et al., Chemistry of indole II. Beckmann and Schmidt Rearrangements of Some Indole Ketones, Chem. Ber., 1970;103(2):496-509.
Database CAOLD on STN, AN CA51:10524d, Hellman et al., N-Mannich bases (VI) condensation of N-dialkylaminomethylbenzamides with amines and amides, (VII) N-acylaminomethylation of indole, Direct Submission, 1953.
Database CAPLUS on STN, AN 1999:325910, Aslanian et al., Preparation of (phenylaiky)imidazoles as H3 receptor antagonists, WO99/24406, 1999.
Database CAPLUS on STN, AN 1977:439214, Misztal et al., Synthesis and pharmacologic properties of pyridoyl derivatives of 3-methylaminoindole 2-methyltryptamine and isotryptamine, Arch Immuno Ther Exp., 1976;24(6):851-62.
Database CAPLUS on STN, AN 1986:68547, Stuetz et al., Synthesis and Structure-activity relationships of naftifine-related allylamine antimycotics, J. Med. Chem., 1986;29(1): 112-25.
Database CAPLUS on STN, AN 1991:428908, Fuse et al., Preparation of cinnamamide derivatives an antihyperlipidemics, EP407200A1, 1991.
Database Crossfile Beilstein, 1966, Database accession No. 2819049, 2819050, XP002216033.
Dykhuizen, Santa Rosalia revisited: Why are there so many species of bacteria? Antonie van Leeuwenhoek, 1998, Kluwer Academic Publishers;73:25-33.
Ettmayer et al., Lessons learned from marketed and investigational prodrugs, J Med Chem. May 6, 2004;47(10):2393-404.

Foroumadi et al., Synthesis and In Vitro Evaluation of N-[5-(5-Nitro-2-Thienyl)-1,3,4-Thiadiazole-2-yl] Piperazinyl Quinolones, European Journal of Medicinal Chemistry. 2003;38:851-4.
Grassberger et al., Preparation and antibacterial activities of new 1,2,3-diazaborine derivatives and analogues, J Med Chem. Aug. 1984;27(8):947-53.
Heath et al., A triclosan-resistant bacterial enzyme, Nature. Jul. 13, 2000;406(6792):145-6.
Heath et al., Regulation of fatty acid elongation and initiation by acyl-acyl carrier protein in *Escherichia coli*. J Biol Chem. Jan. 26, 1996;271(4):1833-6.
Heck, Palladium-Catalyzed Vinylation of Organic Halides, Organic Reactions. 1982;27:345-90.
Heimbach et al., Absorption rate limit considerations for oral phosphate prodrugs, Pharm Res. 2003;20(6):848-856.
Himmler et al., Synthesis and antibacterial in vitro activity of novel analogues of nematophin, Bioorg Med Chem Lett. 1998;8(15):2045-50.
Jossang-Yanagida, Tetrahydropyridoazepines and Tetrahydropyridoazepinones from the Corresponding Dihydroquinolones, J. Heterocyclic Chemistry. 1978;15:249-251.
Kaplan et al, Abstract F1-2006, Correlation of AFN-1252 Phase 0 Microdosing and Phase 1 Pharmacokinetics, American Society for Microbiology $49^{th}$ ICAAC Meeting Abstract, Tuesday, Sep. 15, 2009. 2 pages.
Kaplan and Hafkin, Abstract F1-2005, In Vitro and In Vivo Absorption Properties of AFN-1252, a Novel Specific-Spectrum Anti-Staphylcoccal Agent, American Society for Microbiology $49^{th}$ ICAAC Meeting Abstract, Tuesday, Sep. 15, 2009. 2 pages.
Karchmer et al., Is there a future for FabI inhibitors as antibacterial agents? Clin. Invest. 2013;3(8):707-9.
Karlowsky et al., AFN-1252, a FabI Inhibitor, Demonstrates a *Staphylococcus*-Specific Spectrum of Activity, Antimicrobial Agents and Chemotherapy. 2009;53(8):3544-8.
Karlowsky et al., In vitro activity of API-1252, a novel FabI inhibitor, against clinical isolate of *Staphylococcus aureus* and *Staphylococcus epidermidis*, Antimicrobial Agents and Chemotherapy. 2007;51(4):1580-1.
Kearney et al., The in vitro enzymic labilities of chemically distinct phosphomonoester prodrugs, Pharm Res. Apr. 1992;9(4)497-503.
Leppik et al. Pharmacokinetics and safey of a phenytoin prodrug given i.v. or i.m. in patients, Neurology. Mar. 1990;40(3 Pt 1):456-60.
Levy et al., Molecular basis of triclosan activity, Nature. Apr. 1, 1999;398(6726):383-4.
Li et al., Synthesis and Antistatphyloccocal Activity of Nematophin and its Analogs, Bioorganic & Medicinal Chemistry Letters Oxford, GB, May 20, 1997;7(10):1349-1352.
Lipsky et al., Treating diabetic foot osteomyelitis primarily with surgery or antibiotics: have we answered the question? Diabetes Care. 2014;37(3):593-5. doi: 10.2337/dc13-2510.
Lovati et al., Does $PGE_1$ vasodilator prevent orthopaedic implant-related infection in diabetes? Preliminary results in a mouse model. PLoS One. Apr. 9, 2014;9(4):e94758. doi: 10.1371/journal.pone.0094758. eCollection 2014.
McMurray et al., Triclosan targets lipid synthesis, Nature. Aug. 6, 1998;394(6693):531-2.
Miller et al., Discovery of aminopyridine-based inhibitors of bacterial enoyl-ACP reductase (FabI). J Med Chem. 2002;45(15):3246-3256.
Misztal et al., Synthesis and pharmacologic properties of pyridoyl derivatives of 3-methylaminoindole 2-methyltryptamine and isotryptamine, Arch Immunol Ther Exp (Warsz). 1976;24(6):851-62.
Nicolau et al., Therapeutic options for diabetic foot infections: a review with an emphasis on tissue penetration characteristics. J Am Podiatr Med Assoc. Jan.-Feb. 2010;100(1):52-63. Review.
Pachter et al., The Chemistry of Hortiamine and 6-Methoxyhetsinine, J. Amer. Chem., 1961;83:635-42.
Payne et al., Discovery of a Novel and Potent Class of Fab I-Directed Antibacterial Agents, Am Soc for Microbiology. 2002;46(10):3118-24.

(56) References Cited

OTHER PUBLICATIONS

Payne et al., Bacterial fatty-acid biosynthesis: a genomics-driven target for antibacterial drug discovery. Drug Discov Today. May 1, 2001;6(10):537-544.

Ramnauth et al., 2,3,4,5-Tetrahydro-1H-pyrido[2,3-b and e][1,4]diazepines as inhibitors of the bacterial enoyl ACP reductase, FabI, Bioorganic & Medicinal Chem Letters. 2009;19(18):5359-62.

Rautio et al., Prodrugs: Design and Clinical Applications, Nature Reviews Drug Discovery, 2008;7:255-70.

Rehse et al., Dopaminanaloge 1,2,3,4-Tetrahydro-B-Carboline, Arch. Pharm. 1978;311(1):11-8.

Seefeld et al., Indole naphthyridinones as inhibitors of bacterial enoyl-ACP reductases FabI and FabK, J Med Chem., 2003;46(9):1627-35.

Shoji et al., Two Novel Alkloids from Evodia Rutaecarpa, J. Natural Products, 1989; 52(5):1160-2.

Sladowska et al., Synthesis and properties of amides of 1-benzyl-3-methyl- and 1-butyl-3-phenyl-7-methyl-4-oxo-2-thioxo (2,4-dioxo)-1,2,3,4-tetrahydrophyrido-[2,3-d]pyrimidine-6-carboxylic acids, Farmaco Sci. 1986;41(12):954-63.

Stutz et al., Synthesis and Structure-Activity Relationships of Naftifine-Related Allylamine Antimycotics, Journal of Medicinal Chemistry, 1986;29(1):112-25.

Turnowsky et al., envM genes of *Salmonella typhimurium* and *Escherichia coli*, J Bacteriol. 1989;171(12):6555-65.

Varia et al., Phenytoin Prodrugs III: Water-Soluble Prodrugs for Oral and/or Parenteral Use, J Pharm Sci. 1984;73(8):1068-73.

Varia et al., Phenytoin Prodrugs IV: Hydrolysis of various 3-(hydroxymethyl)phenytoin esters, J Pharm Sci. 1984;73(8):1074-80.

Varia et al., Phenytoin Prodrugs V: In vivo evaluation of some water-soluble phenytoin prodrugs in dogs, J Pharm Sci. 1984;73(8):1080-7.

Varia et al., Phenytoin Prodrugs VI : In vivo evaluation of a phosphate ester prodrug of phenytoin after parenteral administration to rats, J Pharm Sci. 1984;73(8):1087-90.

Ward et al., Kinetic and structural characteristics of the inhibition of enoyl (acyl carrier protein) reductase by triclosan, Biochemistry. 1999;38(38):12514-25.

Banu et al., Spectrum of bacteria associated with diabetic foot ulcer and biofilm formation: A prospective study. Australas Med J. Sep. 30, 2015;8(9):280-5. doi: 10.4066/AMJ.2015.2422. eCollection 2015.

\* cited by examiner

MEDICAMENT FOR TREATMENT OF DIABETIC FOOT INFECTIONS

RELATED APPLICATIONS

This Application is a national stage filing under 35 U.S.C. 371 of International Application Number PCT/EP2017/054470, filed Feb. 27, 2017, and claims priority to European Application Number 16157688.9, filed Feb. 26, 2016, and European Application Number 16157685.5, filed Feb. 26, 2016, each of which is herein incorporated by reference in its entirety.

FIELD OF THE INVENTION

The present invention provides means and methods for treating bacterial infections associated with diabetic foot syndrome or other bacterial infections of the foot associated with peripheral ischemia.

BACKGROUND OF THE INVENTION

The diabetic foot syndrome is a pathology frequently associated with ulceration and bacterial infections. Such bacterial infections are identified herein below as diabetic foot infections. Treatment of diabetic foot infections is frequently hampered by ischemia, which is typically associated with diabetic foot syndrome. Consequently, systemic administration of antibiotics will permit to accomplish only low plasma levels of the antibiotic drug at the site of infection. This problem is particularly severe if the infection is caused by antibiotic-resistant bacteria such as methicillin-resistant *Staphylococcus aureus* (MRSA).

The situation is aggravated further by the fact that diabetic patients frequently suffer from peripheral neuropathy. Such patients may suffer from diabetic foot infections with little or no pain. The infection may remain undetected or may be disregarded by the patient. As a result, infections that usually start in ulcerated soft tissues can spread to underlying bone tissue. Osteomyelitis may develop which is particularly difficult to treat with antibiotic therapy.

Due to the above difficulties, diabetic foot infections are the most common cause for amputation of the lower extremities. Amputation is frequently associated with an increased risk of morbidity and mortality.

There is therefore an urgent need for improved treatments of diabetic foot infections, especially in cases of infections with MRSA and/or in cases where the patient suffers from a significant degree of ischemia and/or in cases where bone tissue is affected.

It is therefore an object of the present invention to provide a compound that permits improved treatment of diabetic foot infections, especially in cases of infections with MRSA and/or in cases where the patient suffers from a significant degree of ischemia and/or in cases where bone tissue is affected.

It is another object of the invention to provide a compound for treating diabetic foot infections, especially diabetic foot osteomyelitis, which permits to increase local concentration of the antibiotic drug at the site of infection.

It is another object of the invention to provide a compound for treating diabetic foot osteomyelitis, which exhibits improved bone penetration.

It is another object of the invention to provide a method of treating diabetic foot infections, especially in cases of infections with MRSA and/or in cases where the patient suffers from a significant degree of ischemia and/or in cases where bone tissue is affected.

It is yet another object of the invention to provide a method of treating diabetic foot infections, especially diabetic foot osteomyelitis, which permits to increase local concentration of the antibiotic drug at the site of infection.

It is also an object of the invention to provide a method of treating diabetic foot osteomyelitis, which relies on the use of a compound that exhibits improved bone penetration.

It is yet another object of the invention to provide a method of treating other bacterial infections of the foot associated with peripheral ischemia.

A further objective is to provide pharmaceutical compositions suitable to the above methods.

SUMMARY OF THE INVENTION

The present invention provides drugs for use in the treatment of diabetic foot infections and other bacterial infections of the foot associated with peripheral ischemia as well as methods for treating such infections. In particular, the present invention provides such drugs as specified in the following numbered embodiments.

1. A compound for use in a method of treating diabetic foot-associated bacterial infections or other bacterial infections of the foot associated with peripheral ischemia, wherein the compound is {6-[(1E)-3-{methyl[(3-methyl-1-benzofuran-2-yl)methyl]amino}-3-oxoprop-1-en-1-yl]-2-oxo-3,4-dihydro-1,8-naphthyridin-1(2H)-yl}methyl dihydrogen phosphate or a pharmaceutically acceptable salt or metabolite or pharmaceutically acceptable salt of a metabolite thereof.
2. The compound for use according to embodiment 1, wherein the bacterial infection is caused by a Staphylococcal species including but not limited to *Staphylococcus aureus*.
3. The compound for use according to embodiment 1 or 2, wherein the bacterial infection is caused by methicillin-resistant *Staphylococcus aureus*.
4. The compound for use according to embodiment 1, 2 or 3, wherein the bacterial infection is an infection of soft tissue and/or bone tissue.
5. The compound for use according to embodiment 1, 2, 3 or 4, wherein the bacterial infection is osteomyelitis.
6. The compound for use according to embodiment 1, 2, 3, 4 or 5, wherein the compound is the bis-ethanolammonium salt of {6-[(1E)-3-{methyl[(3-methyl-1-benzofuran-2-yl)methyl]amino}-3-oxoprop-1-en-1-yl]-2-oxo-3,4-dihydro-1,8-naphthyridin-1(2H)-yl}methyl dihydrogen phosphate.
7. The compound for use according to embodiment 1, 2, 3, 4, 5 or 6, wherein the compound is administered at a dosage of 5 mg/day to 720 mg/day, preferably 40 mg/day to 600 mg/day, more preferably 80 mg/day to 480 mg/day, most preferably 16 mg/day to 480 mg/day.
8. The compound for use according to embodiment 7, wherein the compound is administered intravenously twice daily, each administration being in a dosage of 40 mg to 160 mg.
9. The compound for use according to embodiment 7, wherein the compound is administered orally twice daily, each administration being in a dosage of 40 mg to 240 mg.
10. The compound for use according to embodiment 7, wherein the compound is administered intravenously three times daily, each administration being in a dosage of 40 mg to 240 mg.

11. The compound for use according to embodiment 7, wherein the compound is administered orally three times daily, each administration being in a dosage of 40 mg to 240 mg
12. The compound for use according to embodiment 1, 2, 3, 4, 5, 6, 7, 8, 9, 10 or 11, wherein the method comprises a surgical procedure to remove infected and/or necrotic tissue prior to, simultaneously with and/or after administration of said compound.
13. The compound for use according to embodiment 1, 2, 3, 4, 5, 6, 7, 8, 9, 10, 11 or 12, wherein the method comprises administration of one or more further antibiotic agents or antibacterial agents.
14. A pharmaceutical composition for use in a method of treating diabetic foot-associated bacterial infections or other bacterial infections of the foot associated with peripheral ischemia, wherein the composition comprises the compound specified in embodiment 1 or 6 above and wherein the method is according to one or more of embodiment 1 to 5 and 7 to 13.

DETAILED DESCRIPTION OF THE INVENTION

Definitions

Therapeutically effective dose is used in the context of the present invention to characterize an amount of the drug, which leads to complete or partial eradication of the pathogenic bacterium underlying the diabetic foot infection or other bacterial infection of the foot associated with peripheral ischemia. For instance, any statistically significant reduction in the load of pathogenic bacteria indicates therapeutic efficacy in the context of the present invention.

Pharmaceutically acceptable is used in the context of the present invention to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

Pharmaceutically acceptable salt is used in the context of the present invention to characterize any form of ionic species (acid addition salt, base addition salt, zwitterionic/internal salt, etc.) of the drug, which is pharmaceutically acceptable as defined above.

Diabetes patient is a used in the context of the present invention to characterize a patient suffering from diabetes mellitus as a described in "Diagnosis and Classification of Diabetes Mellitus" by the American Diabetes Association published in Diabetes Care 2004, 27, S5-S10.

Diabetic Foot or Diabetic Foot Syndrome is used in the context of the present invention to characterize a condition as defined by the World Health Organization as "ulceration of the foot (distally from the ankle and including the ankle) associated with neuropathy and different grades of ischemia and infection" (quotation derived from Jeffcoate W. J., Macfarlane R. M., Fletcher E. M. "The description and classification of diabetic foot lesions" in *Diabetic Medicine*, 1993; 10(7):676-679).

Diabetic Foot Infection is used herein to characterize a bacterial infection associated with diabetic foot syndrome.

Diabetic Foot Osteomyelitis is used herein to characterize a bacterial infection of the bone (osteomyelitis), which is associated with diabetic foot syndrome.

Ischemia is described in "Overview of Classification Systems in Peripheral Artery Disease" by R. L. Hardman et al. published in Semin Intervent Radiol 2014; 31:378-388. The term "significant degree of ischemia" may thus be understood as ischemia of grade 1, 2 or 3 as defined in Table 6 of said article "Overview of Classification Systems in Peripheral Artery Disease" by R. L. Hardman et al. published in Semin Intervent Radiol 2014; 31:378-388.

Peripheral ischemia and/or peripheral vascular disease characterize conditions with deficient blood distribution to the limbs caused by narrowing or obstruction of the lumen of the peripheral arteries. The affected limb, here: foot, thus shows ischemia and preferably a significant degree of ischemia as defined above.

Compound A characterizes the compound {6-[(1E)-3-{methyl[(3-methyl-1-benzofuran-2-yl)methyl]amino}-3-oxoprop-1-en-1-yl]-2-oxo-3,4-dihydro-1,8-naphthyridin-1(2H)-yl}methyl dihydrogen phosphate. Other names of this compound are ((E)-6-[(N-methyl-((3-methylbenzofuran-2-yl)methyl)amino)-3-oxoprop-1-en-1-yl)-2-oxo-3,4-dihydro-1,8-naphthyridin-1(2H)-yl]methyl phosphate and (2E)-2-Propenamide, N-methyl-N-[(3-methyl-2-benzofuranyl)methyl]-3-[5,6,7,8-tetrahydro-7-oxo-8-[(phosphonooxy)methyl]-1,8-naphthyridin-3-yl]. Its CAS RN is 1518800-35-5. It is a prodrug. Its active metabolite is identified as Compound B, (E)-N-methyl-N-((3-methylbenzofuran-2-yl)methyl)-3-(7-oxo-5,6,7,8-tetrahydro-1,8-naphthyridin-3-yl)acrylamide. Its CAS RN is 620175-39-5.

The definitions and further information provided herein shall be used for interpreting the claims. In case of any remaining ambiguity, the definitions and information contained in WO 2013/190384 A shall be used on an auxiliary basis and to the extent that they are consistent with the present invention. As a supplementary source of information, chemical, pharmaceutical and medical dictionaries and especially Römpp "Lexikon Chemie", Thieme Verlag 1999; Remington "The Science and Practice of Pharmacy", Pharmaceutical Press, 2012; and "Stedman's Medical Dictionary", Wolters Kluwer, 2006 are to be used as further supplementary sources of information but only to the extent that they are consistent with the information provided herein and in WO 2013/190384 A.

Overview of Invention

Compound A is a drug compound known to be effective in the treatment of bacterial infections and especially those caused by *Staphylococcus aureus*. However, based on the available information, it was not expected that Compound A might be effective in the treatment of diabetic foot infections and especially diabetic foot osteomyelitis.

The present invention is based on the surprising finding that Compound B not only shows antibacterial therapeutic efficacy but additionally exerts vasorelaxant properties. In particular, in preclinical models, Compound B potently inhibits PDE3 enzyme and exerts vasorelaxant properties to the same extent as cilostazol, a drug used in the alleviation of the symptom of intermittent claudication in individuals with peripheral vascular disease. There is a close interrelationship between PDE3 inhibition and vasorelaxant properties since cyclic nucleotide phosphodiesterases (PDEs) are enzymes that regulate the cellular levels of the second messengers, cAMP and cGMP, by controlling their rates of degradation. PDE3A and PDE3B are the subfamily genes of PDE3 that belongs to the 11 related gene families. Inhibition of this enzyme prevents cAMP breakdown and thereby increases its intracellular concentration. Intracellular concentration of cAMP plays an important second messenger role such as regulation of cardiac muscle contraction and vascular smooth muscle contraction (Bender A T, Beavo J A: Cyclic nucleotide phosphodiesterases: molecular regulation to clinical use. Pharmacol. Rev. (2006) 58 (3): 488-520). These properties permit to improve blood perfusion in the affected tissue of diabetic foot patients and other patients suffering from peripheral ischemia. This second therapeutic effect of Compound B provides a key for effective antibiotic treatment of diabetic foot infections because it improves blood perfusion and thus increases local concentration of the drug at the site of infection. The present inventors have furthermore found that Compound B exhibits surprisingly good bone penetration compared to vancomycin in a rabbit model. Bone penetration was found to be particularly high in infected bone. Compound B is therefore particularly effective in the treatment of osteomyelitis associated with diabetic foot. Based on these surprising findings, the present invention has been accomplished.

That is, the present invention provides a compound and pharmaceutical composition for use in the treatment of diabetic foot-associated bacterial infections or other bacterial infections of the foot associated with peripheral ischemia, wherein the compound is specified as described herein. The present invention also provides a method for treating diabetic foot-associated bacterial infections or other bacterial infections of the foot associated with peripheral ischemia, which involves the administration of a therapeutically effective amount of a compound described herein or pharmaceutical composition as described herein to a patient in need thereof.

Drug

Compound A and its synthesis are described in WO 2013/190384 A. The structure of Compound A under its acidic form is shown below:

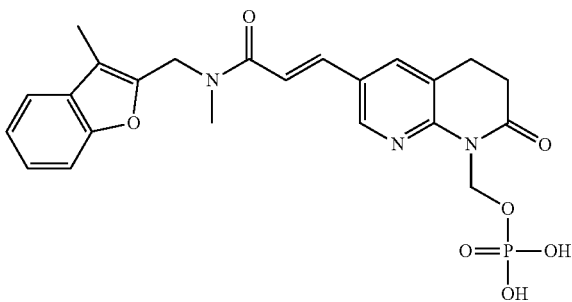 [SMILES: Cc1c(CN(C)C(=O)/C=C/c2cnc3c(c2)CCC(=O)N3COP(=O)(O)O)oc2ccccc12]

Compound A acts as a prodrug of Compound B, a compound described in Example 99 of WO 03/088897 A. The structure of Compound B is shown below:

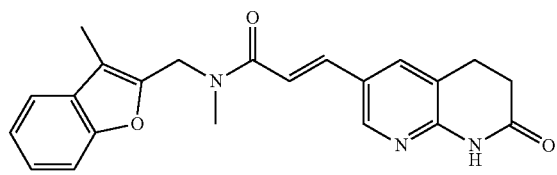 [SMILES: Cc1c(CN(C)C(=O)/C=C/c2cnc3c(c2)CCC(=O)N3)oc2ccccc12]

Compound B acts as an inhibitor of FabI, which is a bacterial target involved in bacterial fatty acid synthesis. Compound B is more difficult to formulate into acceptable parenteral formulations with satisfactory solubility, stability and bioavailability. Therefore, an antibacterial medicament is currently under development based on the prodrug Compound A, which benefits from dual oral and parental formulations.

The present invention relies on the use of Compound A and pharmaceutically acceptable salts thereof. However, in the context of the present invention, it is also possible to use the active metabolite Compound B and pharmaceutically acceptable salts thereof as long as a suitable means of administering the drug can be provided. Insofar, unless the context dictates otherwise, references to Compound A in the present text are to be understood as encompassing also the active metabolite Compound B as well.

Compound A can also be used in the form of a pharmaceutically acceptable salt thereof. Preferred pharmaceutically acceptable salts are disclosed in claims 1 and 6 to 17 of WO 2013/190384 A. Of particular interest is the bis-ethanolammonium salt. However, further pharmaceutically acceptable salts may also be used. Such further pharmaceutically acceptable salts are disclosed, for instance, in S. M. Berge, L. M. Bighley, and D. C. Monkhouse, "Pharmaceutical Salts," J. Pharm. Sci. 66 (1), 1-19 (1977); P. H. Stahl and C. G. Wermuth, editors, *Handbook of Pharmaceutical Salts: Properties, Selection and Use*, Weinheim/Zurich, Wiley-VCH, 2008 and in A. K. Bansal et al., Pharmaceutical Technology, 3(32), 2008.

It is furthermore possible to use combinations of Compound A with one or more other drugs and especially antibiotic drugs. Suitable co-drugs are listed in paragraphs [00131]-[00140] and claims 32-34 of WO 2013/190384 A. Specific co-drugs, including those mentioned in WO 2013/190384 A, are listed below.

Possible co-drugs include other FabI inhibitors, other antibiotic agents or antibacterial agents as described below.

Non-limiting examples of antibiotic agents that may be used as co-drugs include cephalosporins, quinolones and fluoroquinolones, penicillins, penicillins and beta lactamase inhibitors, carbepenems, monobactams, macrolides and lincosamines, glycopeptides, lipopeptides, lipoglycopeptides, rifamycin, oxazolidonones, tetracyclines, aminoglycosides, streptogramins, sulfonamides, and others. Each family comprises many members.

Cephalosporins can be further categorized by generation. Suitable non-limiting examples of cephalosporins by generation include the following. Examples of cephalosporins—First generation compounds include Cefadroxil, Cefazolin, Cefalexin, Cefalothin, Cefapirin and Cephradine. Second generation compounds include Cefaclor, Cefamandole, Cefonicid, Cefotetan, Cefoxitin, Cefprozil, Ceftmetazole, Cefuroxime, Cefuroxime axetil, and Loracarbef.— Third generation include Cefdinir, Ceftibuten, Cefditoren, Cefetamet, Cefbodoxime, Cefprozil, Cefuroxime (axetil), Cefuroxime (sodium), Cefoperazone, Cefixime, Cefotaxime, Cefpodoxime proxetil, Ceftazidime, Ceftizoxime, Cefcapene, Cefdaloxime, Cefmenoxime, Cefpiramide, and Ceftriaxone. Fourth generation compounds include Cefepime. Fifth generation compounds include Ceftaroline fosamil, Ceftolozane and Ceftobiprole.

Non-limiting examples of suitable quinolones and fluoroquinolones include Cinoxacin, Ciprofloxacin, Enoxacin, Gatifloxacin, Grepafloxacin, Levofloxacin, Lomefloxacin, Besifloxacin, Finafloxacin, Moxifloxacin, Nalidixic acid, Norfloxacin, Ofloxacin, Sparfloxacin, Trovafloxacin, Oxolinic acid, Gemifloxacin, Pefloxacin and Nemonoxacin and Novobiocin.

Non-limiting examples of suitable penicillins include Amoxicillin, Ampicillin, Bacampicillin, Carbenicillin Indanyl, Mezlocillin, Piperacillin, and Ticarcillin.

Non-limiting examples of suitable penicillins and beta lactamase inhibitors include Amoxicillin-Clavulanic Acid, Ampicillin-Sulbactam, Benzylpenicillin, Cloxacillin Dicloxacillin, Methicillin, Oxacillin, Penicillin G (Benzathine, Potassium, Procaine), Penicillin V, Piperacillin+Tazobactam, Ticarcillin+Clavulanic Acid, and Nafcillin.

Non-limiting examples of suitable carbepenems include Doripenem, Ertapenem, Imipenem-Cilastatin and Meropenem. A non-limiting example of a suitable monobactam includes Aztreonam. Non-limiting examples of suitable macrolides and lincosamines include Azithromycin, Clarithromycin, Clindamycin, Dirithromycin, Erythromycin, Lincomycin, Flurithromycin, Josamycin, Midecamycin, Miocamycin, Oleandomycin, Rokitamycin, Roxithromycin, Spiramycin, Tylosin, Ketolides, Pirlimycin and Troleandomycin. Non-limiting examples of suitable glycopeptides include Teicoplanin, Dalbavancin, Ramoplanin, Vancomycin, Oritavancin and Telavancin. Non-limiting examples of suitable rifampins include Rifabutin, Rifampin, and Rifapentine. A non-limiting example of suitable oxazolidonones includes Linezolid, Eperezolid, Posizolid, Radelozid, Ranbezolid, Sutezolid, Tedizolid. Non-limiting examples of suitable tetracyclines include Demeclocycline, Doxycycline, Metacycline, Minocycline, Oxytetracycline, Tetracycline, Clomocycline, Lymecycline, Meclocycline, Penimepicycline, Rolitetracycline, Tigecycline and Chlortetracycline.

Non-limiting examples of suitable aminoglycosides include Amikacin, Arbakacin, Gentamicin, Kanamycin, Sisomicin, Arbekacin, Neomycin, Netilmicin, Streptomycin, Tobramycin, Bekanamycin, Ribostamycin, Spectinomycin, Hygromycin B, Dihydrostreptomycin, Verdamicin, Astromicin and Paromomycin. A non-limiting example of suitable streptogramins includes Quinopristin+Dalfopristin, Pristinamycin and Virginiamycin.

Non-limiting examples of suitable sulfonamides include Mafenide, Silver Sulfadiazine, Sulfacetamide, Sulfadiazine, Sulfamethoxazole, Sulfasalazine, Sulfisoxazole, Trimethoprim-Sulfamethoxazole, Sulfamethizole, Sulfaisodimidine, Sulfamethizole, Sulfadimidine, Sulfapyridine, Sulfafurazole, Sulfanilamide, Sulfathiazole, Sulfathiourea, Sulfamoxole, Sulfadimethoxine, Sulfadoxine, Sulfalene, Sulfametomidine, Sulfamethoxydiazine, Sulfamethoxypyradazine, Sullfaperin, Sulfamerazine, Sulfaphenazole, Sulfamazone.

Non-limiting examples of suitable other antibiotic agents include Bacitracin, Chloramphenicol, Azidamfenicol, Thiamphenicol, Florfenicol, Retapamulin, Tiamulin, Valnemulin, Fusidic Acid, Colistimethate, Fosfomycin, Isoniazid, Methenamine, Metronidazole, Tinidazole, Omidazole, Mupirocin, Nitrofurantoin, Nitrofurazone, Nifurtoinol, Novobiocin, Polymyxin B, Spectinomycin, Tobramycin, Tigecycline, Trimethoprim, Brodimoprim, Tetroxoprim, Colistin, Polymyxin B, Daptomycin, Gramicidin, Isioniazid, Teixobactin, Cycloserine, Capreomycin, Pyrazinamide, para-Aminosalicyclic acid, and Erythromycin ethylsuccinate+sulfisoxazole.

If it is decided to use a drug combination, the subsequent indications regarding administration form dosage, etc. need to be suitably adapted taking the characteristics of the co-drug into account. The one or more co-drugs mentioned above can be administered prior to, simultaneously with and/or after administration of the compound A or pharmaceutically acceptable salt or metabolite (e.g. compound B) or pharmaceutically acceptable salt of a metabolite thereof.

Drug Formulation, Administration and Dosage

Compound A may be formulated and administered as described in paragraphs [00141] to [00164] of WO 2013/190384 A. Preferred formulations are formulations suitable for intravenous administration and formulations suitable for oral administration. Particularly suitable are the following types of the formulations: tablets, capsules, liquid solutions and suspensions for oral administration. For parenteral administration, sterile solutions and suspensions for injection can be prepared using standard excipients. Specific formulation types of interest among those described in WO 2013/190384 A are recited below.

Pharmaceutical compositions of the disclosure may be administered by various means, depending on their intended use, as is well known in the art. For example, if compositions of the disclosure are to be administered orally, they may be formulated as tablets, capsules, granules, powders or syrups. Alternatively, formulations disclosed herein may be administered parenterally as injections (intravenous, intramuscular or subcutaneous), drop infusion preparations.

These formulations may be prepared by conventional means, and, if desired, the compositions may be mixed with any conventional additive, such as an excipient, a binder, a disintegrating agent, a lubricant, a corrigent, a solubilizing agent, a suspension aid, an emulsifying agent or a coating agent. The disclosed excipients may serve more than one function. For example, fillers or binders may also be disintegrants, glidants, anti-adherents, lubricants, sweeteners and the like.

In formulations of the disclosure, wetting agents, emulsifiers and lubricants, such as sodium lauryl sulfate and magnesium stearate, as well as coloring agents, release agents, coating agents, sweetening, flavoring and perfuming agents, preservatives and antioxidants may be present in the formulated agents.

Subject compositions may be suitable for oral, nasal (e.g., by inhalation using a dry powder formulation or a nebulized formulation), topical (including buccal and sublingual), pulmonary (including aerosol administration), aerosol and/or parenteral (e.g., by injection, for example, intravenous or subcutaneous injection) administration. The formulations may conveniently be presented in unit dosage form and may be prepared by any methods known in the art of pharmacy. The amount of a composition that may be combined with a carrier material to produce a single dose vary depending upon the subject being treated, and the particular mode of administration.

Methods of preparing these formulations include the step of bringing into association compositions of the disclosure with the carrier and, optionally, one or more accessory ingredients. In general, the formulations are prepared by uniformly and intimately bringing into association agents with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a subject composition thereof as an active ingredient. Compositions of the disclosure may also be administered as a bolus, electuary, or paste.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, dextrose, lactose, sucrose, glucose, mannitol, and/or silicic acid; (2) binders, such as, for example, celluloses (e.g., microcrystalline cellulose, methyl cellulose, hydroxypropylmethyl cellulose (HPMC) and carboxymethylcellulose), alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like. The disclosed excipients may serve more than one function. For example, fillers or binders may also be disintegrants, glidants, anti-adherents, lubricants, sweeteners and the like.

Formulations and compositions may include micronized crystals of the disclosed compounds. Micronization may be performed on crystals of the compounds alone, or on a mixture of crystals and a part or whole of pharmaceutical excipients or carriers. Mean particle size of micronized crystals of a disclosed compound may be for example about 5 to about 200 microns, or about 10 to about 1 10 microns.

A tablet may be made by compression or molding, optionally with one or more accessory ingredients. Compressed tablets may be prepared using binder (for example, gelatin, microcrystalline cellulose, or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

It will be appreciated that a disclosed composition may include lyophilized or freeze dried compounds disclosed herein. For example, disclosed herein are compositions that disclosed compounds crystalline and/or amorphous powder forms.

Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for transdermal administration of a subject composition includes powders, sprays, ointments, pastes, creams, lotions, gels, solutions, and patches. The active component may be mixed under sterile conditions with a pharmaceutically acceptable carrier, and with any preservatives, buffers, or propellants that may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds of the disclosure may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions.

Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

It should be noted that excipients given as examples may have more than one function. For example, fillers or binders can also be disintegrants, glidants, anti-adherents, lubricants, sweeteners and the like.

Pharmaceutical compositions of this disclosure suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. For example, provided herein is an aqueous composition that includes a disclosed compound, and may further include for example, dextrose (e.g., about 1 to about 10 weight percent dextrose, or about 5 weight percent dextrose in water (D5W).

Examples of suitable aqueous and non-aqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants.

It will be appreciated that contemplated formulations, such as oral formulations (e.g. a pill or tablet), may be formulated as controlled release formulation, e.g., an immediate release formulation, a delayed release formulation, or a combination thereof.

In certain embodiments, the subject compounds may be formulated as a tablet, pill, capsule or other appropriate ingestible formulation (collectively hereinafter "tablet"). In certain embodiments, a therapeutic dose may be provided in 10 tablets or fewer. In another example, a therapeutic dose is provided in 50, 40, 30, 20, 15, 10, 5 or 3 tablets.

In a certain embodiment, a disclosed compound is formulated for oral administration as a tablet, capsule, or an aqueous solution or suspension. In another embodiment of a tablet form the tablets are formulated such that the resulting amount of antibacterial agent (or antibacterial agents), if taken together (e.g., over time) once administered, would provide a dose of at least the median effective dose ($ED_{50}$), e.g., the dose at which at least 50% of individuals exhibited the quantal effect of inhibition of bacterial cell growth or protection (e.g., a statistically significant reduction in infection). In a further embodiment, tablets may be formulated such that the total amount of antibacterial agent (or antibacterial agents) provided upon administration would provide at least an $ED_{50}$ dose to a patient (human or non-human mammal). In other embodiments, the amount of antibacterial agent (or antibacterial agents) provided, taken in a 24 hour time period would provide a dosage regimen providing, on average, a mean plasma level of the antibacterial agent(s) of at least the $ED_{50}$ concentration (the concentration for 50% of maximal effect of, e.g., inhibiting bacterial cell growth). In other embodiments less than 100 times, 10 times, or 5 times the $ED_{50}$ is provided. In other embodiments, a single dose provides about 0.25 mg to 1250 mg of compound(s).

Likewise, compounds disclosed herein can be formulated for parenteral administration, as for example, for subcutaneous, intramuscular or intravenous injection, e.g., the antibacterial agent can be provided in a sterile solution or suspension (collectively hereinafter "injectable solution"). The injectable solution may be, in some embodiments, formulated such that the amount of antibacterial agent (or antibacterial agents) provided in, for example, bolus injection, or a dose administered intravenously, would provide a dose of at least the median effective dose, or less than 100 times the $ED_{50}$, or less than 10 or 5 times the $ED_{50}$. The injectable solution may be formulated such that the total amount of antibacterial agent (or antibacterial agents) provided (upon administration) would provide an $ED_{50}$ dose to a patient, or less than 100 times the $ED_{50}$, or less than 10 or 5 times the $ED_{50}$. In other embodiments, the amount of antibacterial agent (or antibacterial agents) provided, upon administration, to be injected at least twice in a 24 hour time period would provide a dosage regimen providing, on average, a mean plasma level of the antibacterial agent(s) of at least the $ED_{50}$ concentration, or less than 100 times the $ED_{50}$, or less than 10 or 5 times the $ED_{50}$. In other embodiments, a single dose injection provides about 0.25 mg to 1250 mg, or about 0.25 mg to about 2500 mg of antibacterial agent.

The dosage of Compound A is not particularly restricted and may be suitably selected by the treating physician depending on the condition of the patient. Compound A can be administered in a dosage of 5 mg/day to 720 mg/day, preferably 40 mg/day to 600 mg/day, more preferably 80 mg/day to 480 mg/day, most preferably 16 mg/day to 480 mg/day. Preferred to dosages are furthermore 80 mg/day to 480 mg/day or 80 mg/day-320 mg/day, more preferably 160 mg/day-320 mg/day or 100-300 mg/day, most preferably about 200 mg/day to 240 mg/day for intravenous administration and 80 mg/day to 720 mg/day or 80 mg/day-480 mg/day, more preferably 240 mg/day to 480 mg/day or 100 mg/day-450 mg/day, most preferably about 280 mg/day to 320 mg/day for oral administration. These dosages can be administered by continuous infusion, by once a day dosing or by multiple dosages like twice a day, 3 times a day, 4 times a day, etc. This means that a preferred dosage regimen is 40 mg BID to 160 mg BID or TID by intravenous administration and 40 mg BID to 240 mg BID or TID for oral administration. In another embodiment, the dosages can be administered in greater time intervals such as every other day or once a week. Possible time intervals include especially 2 days, 3 days, 4 days, 5 days, 6 days, 7 days, 10 days and 14 days. Such longer time intervals may for instance be suitable for the IV administration of nanosuspensions. Dosage indications provided herein refer to the free acid form of Compound A. If a Compound B or salt forms of Compound A or Compound B are used, dosages must be adapted by multiplying the above dosage indications with the ratio of molecular weight of the selected compound to the molecular weight of Compound A.

The duration of the administration of Compound A is not particularly limited. In many instances, it will be advantageous to continue the administration of a Compound A for a duration of 2 weeks to 16 weeks or 2 weeks to 13 weeks, more preferably 4 weeks to 14 weeks of 4 weeks to 10 weeks, most preferably 6 weeks to 12 weeks.

The present invention thus relates inter alia to a method of treating diabetic foot-associated bacterial infections or other bacterial infections of the foot associated with peripheral ischemia in a patient in need thereof, wherein the method comprises administering a therapeutically effective amount, e.g. as specified in the preceding paragraphs of this section, of {6-[(1E)-3-{methyl[(3-methyl-1-benzofuran-2-yl)methyl]amino}-3-oxoprop-1-en-1-yl]-2-oxo-3,4-dihydro-1,8-naphthyridin-1(2H)-yl}methyl dihydrogen phosphate or a pharmaceutically acceptable salt or metabolite or pharmaceutically acceptable salt of a metabolite thereof to said patient. The method may further comprise a surgical procedure to remove infected and/or necrotic tissue prior to, simultaneously with and/or after administration of said compound.

Patients

The patients to be treated are patients with peripheral ischemia suffering from foot infection and especially human diabetes patients suffering from diabetic foot infection or other bacterial infections of the foot associated with peripheral ischemia and in particular patients suffering from diabetic foot infection with or without diabetic foot osteomyelitis. The infection may be caused by a single strain of pathogenic bacteria but it could also be caused by a multiplicity of such bacteria strains. In particular, the present invention pertains to means and methods for treating patients suffering from infections of the foot such as diabetic foot infections, which are caused by one or more of the following bacteria:

*Staphylococcus* species

*Staphylococcus* species resistant to antibiotics commonly used to treat infections caused by gram-positive bacteria including but not limited to β-lactams such us penicillins (e.g. oxacillin, ampicillin) and cephalosporins (e.g. cefazolin, ceftaroline), vancomycin, linezolid, clindamycin, rifampicin, daptomycin, fluoroquinolones such as levofloxacin and ciprofloxacin, trimethoprim/sulfamethoxazole, fosfomycin, fusidic acid, tigecycline, and tetracyclines such as doxycycline

*Staphylococcus aureus*

Community-acquired *Staphylococcus aureus*

Hospital-acquired *Staphylococcus aureus*

Methicillin-susceptible *Staphylococcus aureus*

Methicillin-resistant *Staphylococcus aureus*

*Staphylococcus aureus* strains resistant to antibiotics commonly used to treat infections caused by gram-positive bacteria including but not limited to β-lactams such us penicillins (e.g. oxacillin, ampicillin) and cephalosporins (e.g. cefazolin, ceftarolin), vancomycin, linezolid, clindamycin, rifampicin, daptomycin, fluoroquinolones such as levofloxacin and ciprofloxacin, trimethoprim/sulfamethoxazole, fosfomycin, fusidic acid, tigecycline, and tetracyclines such as doxycycline Multidrug resistant *Staphylococcus aureus* strains Coagulase negative Staphylococci Coagulase negative Staphylococci strains resistant to antibiotics commonly used to treat infections caused by gram-positive bacteria including but not limited to β-lactams such us penicillins (e.g. oxacillin, ampicillin) and cephalosporins (e.g. cefazolin, ceftarolin), vancomycin, linezolid, clindamycin, rifampicin, daptomycin, fluoroquinolones such as levofloxacin and ciprofloxacin, trimethoprim/sulfamethoxazole, fosfomycin, fusidic acid, tigecycline, and tetracyclines such as doxycycline

*Staphylococcus epidermidis*

Methicillin-resistant *Staphylococcus epidermidis*

Methicillin-susceptible *Staphylococcus epidermidis*

*Staphylococcus epidermidis* strains resistant to antibiotics commonly used to treat infections caused by gram-positive bacteria including but not limited to β-lactams such us penicillins (e.g. oxacillin, ampicillin) and cephalosporins (e.g. cefazolin, ceftarolin), vancomycin, linezolid, clindamycin, rifampicin, daptomycin, fluoroquinolones such as levofloxacin and ciprofloxacin, trimethoprim/sulfamethoxazole, fosfomycin, fusidic acid, tigecycline, and tetracyclines such as doxycycline Multidrug resistant *Staphylococcus epidermidis* strains

*Staphylococcus haemolyticus*

*Staphylococcus lugdunensis*

*Staphylococcus simulans*

*Staphylococcus hominis*

The compounds and pharmaceutical compositions of the present invention are particularly suitable for the treatment of patients suffering from foot osteomyelitis such as diabetic foot osteomyelitis, which is associated with a significant degree of ischemia in the foot tissue, such as the diabetic foot tissue. The vasorelaxant properties of the compounds of the present invention are particularly beneficial in such patients. In this connection, the term "significant degree of ischemia" refers to a degree of blood perfusion in the infected bone tissue that is 50% or less, preferably 30% or less of the degree of blood perfusion in soft and/or bone tissue of unaffected body parts of the same patient (e.g. the patient's hands). Alternatively, "significant degree of ischemia" may also be understood as ischemia of grade 1, 2 or 3 as defined in Table 6 of "Overview of Classification Systems in Peripheral Artery Disease" by R. L. Hardman et al. published in Semin Intervent Radiol 2014; 31:378-388.

In one embodiment, the treatment is administered to patients who are neither planning to have children nor are in the process of having children.

Preferred Embodiment

It is a preferred embodiment of the present invention to use Compound A or its pharmaceutically acceptable salts in the treatment of diabetic foot osteomyelitis. It is a particularly preferred aspect of this preferred embodiment to use the bis-ethanolammonium salt of Compound A. It is also a particularly preferred aspect of this preferred embodiment to treat diabetic foot osteomyelitis caused by a *Staphylococcus aureus* infection. It is also a particularly preferred aspect of this preferred embodiment to treat diabetic foot osteomyelitis associated with a significant degree of ischemia. It is yet another particularly preferred embodiment to administer Compound A in a dose range of 40 mg BID to 160 mg BID or TID by intravenous administration or 40 mg BID to 240 mg BID or TID by oral administration. Even more preferred embodiments are characterized by the simultaneous fulfillment of two or more of these particularly preferred aspects.

EXAMPLES

Example 1—PDE3 Inhibition Assay

Introduction:

Cyclic nucleotide phosphodiesterases (PDEs) are enzymes that regulate the cellular levels of the second messengers, cAMP and cGMP, by controlling their rates of degradation. PDE3A and PDE3B are members of PDE3 family. Inhibition of PDE3 prevents cAMP breakdown and thereby increases its intracellular concentration. Intracellular concentration of cAMP plays an important second messenger role such as regulation of cardiac muscle contraction and vascular smooth muscle contraction (1. Bender A T, Beavo J A: Cyclic nucleotide phosphodiesterases: molecular regulation to clinical use. Pharmacol. Rev. (2006) 58 (3): 488-520.)

Materials/Methods:

The inhibitory activity of Compound B was assessed against human PDE3A and PDE3B and was compared to cilostazol (a PDE3 inhibitor) in the enzymatic phosphodiesterase assay using Caliper mobility shift assay (2. Card A1, Caldwell C, Min H et al: High-throughput biochemical kinase selectivity assays: panel development and screening applications. J Biomol Screen. (2009); 14(1):31-42.). This method is based on change in charge and electrophoretic separation of product from fluorescently labeled substrate iFL-cAMP. Assays were performed in a 26 µL volume in a 384 well plate. iFL-cAMP substrate was incubated, off-chip, in reaction buffer (100 mM HEPES (pH 7.5), 5 mM $MgCl_2$ and 0.002% Brij35) in the presence of active enzymes (PDE3A and PDE3B) and test compounds at various concentrations. After incubation period, the reaction products and remaining substrate were measured. Detection was performed using EZ reader II. The concentration of compound inducing 50% of the response ($IC_{50}$) was determined from each individual concentration-response curve using variable slope fits with Prism software (Graph Pad, San Diego, Calif., USA).

Results:

The PDE3 inhibitor cilostazol inhibited the enzymatic activity of both isoforms and appeared to be slightly more potent on PDE3A than PDE3B, with the respective absolute $IC_{50}$ values of 0.416 µM and 0.912 µM. Compound B was also able to inhibit both PDE3A and PDE3B enzymatic activities with respective absolute $IC_{50}$ values of 0.6 µM and 0.703 µM, respectively Conclusion:

Compound B inhibitory activity on PDE3A and PDE3B was comparable to that of cilostazol, a drug used in the alleviation of the symptom of intermittent claudication in individuals with peripheral vascular disease.

Example 2—In Vitro Vascular Relaxation Test in Rabbit Saphenous Vein Model

Materials/Methods:

The vascular relaxing effects of Compound B were evaluated using isolated rabbit saphenous venous tissue. Rabbits were sacrificed by a blow to the head followed by a cervical dislocation and exsanguination. A segment of the saphenous vein was carefully excised. Vein was cleaned of all fat and connective tissue and cut into 2.5 mm long rings. The rings were then mounted horizontally in 20-ml organ baths filled with Krebs's solution maintained at 37.7±0.5° C. and gassed with a mixture of 95% $O_2$ and 5% $CO_2$. Krebs's solution was made up as follows (mM): NaCl: 118.0/KCl: 5.0/$CaCl_2$): 2.6/$MgSO_4$ ($7H_2O$): 1.2/$NaHCO_3$: 24.9/$KH_2PO_4$: 1.2/glucose: 10.0. pH is 7.40±0.05. The rings were allowed to equilibrate for 60 minutes at an optimal resting tension of 1 g. Contractile tensions were measured using an isometric force transducer and signals were analyzed using a specialized software (IOX version 1.554, EMKA Technologies, Paris, France). Tissue viability was verified using three challenges to 80 mM KCl. The maximal contraction was reached after 3 challenges of KCl. Endothelium integrity was verified on the basis of the relaxation produced by 1 µM acetylcholine in rings precontracted with 1 µM noradrenaline. All experiments were performed on arterial rings with endothelium. The method evaluated the effect of the test substance in pre-contracted preparations. The preparations were pre-contracted with an agonist (Noradrenaline at 1 µM) until a stable tonic contraction was reached. Six cumulative concentrations of the test or comparison substances were then added into the bath and relaxations were recorded to plot a concentration-response curve. Three preparations were exposed to DMSO, 0.1% over 6 consecutive periods for comparison to Compound B and cilostazol. Four preparations (obtained from 4 animals) were studied for the test and comparison substances. Three preparations were studied for the DMSO-treated group. The relaxation response to test substance was expressed as the percentage of inhibition of agonist-induced pre-contraction. The concentration of agonist inducing 50% of the maximum response ($EC_{50}$) was determined from each individual concentration-response curve using linear regression. For each ring, the agonist potency ($pD_2$) was calculated as –log ($EC_{50}$).

Results:

Viability of the venous preparations and integrity of the endothelium were verified (KCl-induced contraction: in mean±SD 3.90±0.05; 4.29±0.2 and 4.32±0.29 g, respectively, for DMSO-, Compound B- and cilostazol-treated groups and acetylcholine-induced relaxation in mean±SD–93±3, –62±11 and –82±6%, respectively for DMSO-, Compound B- and cilostazol-treated groups).

In the rabbit saphenous vein rings pre-contracted with 1 µM noradrenaline, DMSO (0.1% over 6 consecutive periods) caused a progressive relaxation of the preparation over the time (maximal relaxation of –29±11%).

From 0.03 to 1 µM, Compound B had no relaxant effects on the saphenous vein rings pre-contracted with 1 µM noradrenaline, as compared to vehicle control group (DMSO). In contrast, at 3 and 10 µM, Compound B concentration-dependently relaxed the 1 µM noradrenaline pre-contracted preparations (–69±9% at 10 µM versus –29±11% in the DMSO-treated group, $pD_2$ value=5.85±0.10).

From 0.001 to 1 µM, cilostazol had no relaxant effects on the saphenous vein rings pre-contracted with 1 µM noradrenaline, as compared to vehicle control group (DMSO). In contrast, at 10 and 100 µM, cilostazol concentration-dependently relaxed the 1 µM noradrenaline pre-contracted preparations (–70±7% at 100 µM versus –29±11% in the DMSO-treated group, pD2 value=6.08±0.14).

Conclusion:

3 and 10 µM Compound B exerted vasorelaxant properties on 1 µM noradrenaline pre-contracted rabbit saphenous vein rings. For comparison, cilostazol showed vasorelaxant properties on pre-contracted saphenous vein rings at 10 and 100 µM.

Example 3—In Vivo Treatment of *Staphylococcus aureus*-Induced Acute Osteomyelitis in a Rat Model Materials/Methods:

Minimum inhibitory concentration (MIC) assays were performed by broth microdilution using CLSI guidelines against 20 MRSA strains isolated from bone infections. Experimental osteomyelitis was induced through inoculation of the tibial medullary cavity with 7 $\log_{10}$ colony-forming unit (CFU) of a Panton-Valentine leukocidin (PVL)-positive MRSA strain on day 1. Animals were randomly assigned to the following treatment groups: Compound A 100 mg/kg po BID, vancomycin 100 mg/kg ip QD, fosfomycin 75 mg/kg ip QD and vehicle po BID for 3 weeks starting on day 8 post infection (n=6/group). CFU were enumerated in bone homogenates prior to treatment on day 8 in control animals and at the end of treatment period on day 28. Infected and non-infected bone and plasma samples were collected for quantification of Compound B by LC-MS/MS.

Results:

Compound B was found to be extremely active against all of the 20 MRSA bone isolates including 5 clindamycin-resistant and 2 PVL-positive strains with a very tight MIC range from 0.004 to 0.015 µg/ml. In rats with experimental osteomyelitis, quantitative cultures from bone were found positive for MRSA in all control animals prior to treatment on day 8 (median: 5.8 $\log_{10}$ CFU/g of bone) and in all vehicle-treated animals on day 28 (5.6 $\log_{10}$ CFU/g of bone). Bone cultures were found negative in 0/6 rats for the vancomycin group and 2/6 (33%) rats for Compound A or fosfomycin groups. Compound A and fosfomycin treatment induced a mean 2.8 (p<0.005) and 3.3 (p<0.003) $\log_{10}$ CFU/g of bone reduction in bacterial burden compared to vehicle controls on day 8 (Mann-Whitney test). Rats treated with vancomycin had no statistically significant reduction in bacterial burden. No development of resistance against Compound A was observed after the 3-week treatment period. The bone:plasma ratio of Compound B ranged between 0.06 to 0.27 with no difference between infected and non-infected tibias.

Conclusion:

Together, experimental osteomyelitis efficacy and drug bone penetration results suggest that Compound A has therapeutic potential in the treatment of staphylococcal osteomyelitis.

Example 4—In Vivo Treatment of *Staphylococcus aureus*-Induced Acute Osteomyelitis in a Rabbit Model (1)

Materials/Methods:

MIC assays were performed by broth microdilution using CLSI guidelines. Osteomyelitis (OM) was induced in rabbit through inoculation of the knee with $10^8$ CFU of an MRSA clinical strain after bone trepanation. On day 3 post-inoculation, surgical debridement was performed to mimic the clinical procedure. Samples of femoral red bone marrow (BM) and epiphyseal spongy bone were removed and bacterial counts were determined.

Treatments were started on day 3 post inoculation and lasted for 4 days with selected doses, which approximated an equivalent therapeutic exposure in human: Compound A 12.5 mg/kg BID iv (4 h infusion) approximating a human dose of 160 mg IV BID, or 320 mg/day or its vehicle BID iv, or vancomycin 100 mg/kg once daily constant iv infusion to reach a serum steady-state concentration of 20× the MIC (approximating a human dose of 30 mg/kg given once daily). On day 7 post-inoculation, the bacterial counts were determined in BM and bone samples. The treatment efficacy was assessed by comparing the bacterial counts before (day 3 after infection) and after (day 7 after infection) the antibacterial therapy. Infected and non-infected BM, bone and plasma samples were collected for quantification of Compound B by LC-MS/MS.

Results:

MICs for the MRSA isolate were 0.004 μg/ml for Compound B and 1 μg/ml for vancomycin. The in vivo outcomes are shown in the Table 1. Compound A demonstrated a significant anti-staphylococcal activity in BM and bone. No significant difference in bacterial counts was observed between vancomycin and vehicle. No development of resistance against Compound B was observed after the 4-day treatment period. As shown in Table 2, Compound B presented a high bone penetration with higher bone and bone marrow to plasma ratios in infected tissues than in non-infected tissues. Mean±SD ratios were 2.1±1.35 and 1.8±3.6 in infected bones and bone marrows respectively.

TABLE 1

Mean change in bacterial counts in bone marrow and bone tissues after 4 days of treatment.

| Treatment (number of animals) | Mean ± SD $\Delta\log_{10}$ CFU/g of tissue (day 3-day 7) | |
|---|---|---|
| | Bone marrow | Epiphyseal bone |
| Vehicle (5) | 0.43 ± 0.58 | 0.27 ± 0.60 |
| Compound A (10) | −3.62 ± 0.67* | −2.52 ± 1.25* |
| Vancomycin (6) | −1.05 ± 1.30 | −0.49 ± 0.65 |

*p < 0.001 vs vehicle and vancomycin (analysis of variance (ANOVA) followed by a Student-Newman-Keuls test).

TABLE 2

Drug bone and bone marrow to plasma ratios (n = 10)

| Compound A (12.5 mg/kg) | Ratio bone infected | Ratio bone not infected | Ratio bone marrow infected | Ratio bone marrow not infected |
|---|---|---|---|---|
| Mean ± SD | 2.1 ± 1.35 | 0.30 ± 0.13 | 1.80 ± 3.6 | 0.31 ± 0.14 |
| Median | 1.84 | 0.35 | 0.49 | 0.33 |
| Min-Max | 0.44-4.80 | <0.31-0.44 | <0.31-12 | <0.31-0.52 |

Conclusion:

In conclusion, experimental OM efficacy and drug bone penetration results suggest that Compound A has a therapeutic potential in the treatment of staphylococcal OM.

Example 5—In Vivo Treatment of *Staphylococcus aureus*-Induced Acute Osteomyelitis in a Rabbit Model (2)

Materials/Methods:

MIC assays were performed by broth microdilution using CLSI guidelines. OM was induced in rabbit through inoculation of the knee with $10^8$ CFU/mL of a MRSA clinical strain after bone trepanation. On day 3 post-inoculation, surgical debridement was performed to mimic the clinical procedure. Samples of femoral red bone marrow (BM) and epiphyseal spongy bone were removed and bacterial counts corresponding to day 3 after infection were determined. Treatments were started after 3 days of infection and lasted for 4 days with compound A at the dose level of 12.5, 6.25, 1.6, 0.4 or 0.1 mg/kg BID iv (4 h infusion) or its vehicle BID iv. On day 7 post-inoculation, the bacterial counts were determined in BM and bone samples. The treatment efficacy was assessed by comparing the bacterial counts before (day 3 after infection) and after (day 7 after infection) the antibacterial therapy.

Results:

MICs for the MRSA isolate were 0.004 μg/ml for Compound B. The in vivo outcomes are shown in the Table 3. Compound A at 12.5 mg/kg demonstrated a significant reduction in bacterial titers in BM and bone. The assessment of lower doses of Compound A (6.25, 1.6, 0.4 and 0.1 mg/kg IV BID) showed a dose-effect relationship and a significant reduction in bacterial counts in BM and bone down to the 0.4 mg/kg dose. No development of resistance against Compound B was observed after the 4-day treatment period.

TABLE 3

Mean change in bacterial counts in bone marrow and bone tissues after 4 days of treatment.

| Treatment (number of animals) | Mean ± SD $\Delta\log_{10}$ CFU/g of tissue (day 3-day 7) | |
|---|---|---|
| | Bone marrow | Epiphyseal bone |
| Vehicle (5% Dextrose) BID iv (8) | 0.36 ± 0.54 | 0.18 ± 0.51 |
| Compound A 12.5 mg/kg BID iv (11) | −3.42 ± 0.96 [a] | −1.76 ± 0.74 [a] |
| Compound A 6.25 mg/kg BID iv (9) | −3.45 ± 1.53 [a] | −2.17 ± 0.72 [a] |
| Compound A 1.6 mg/kg BID iv (6) | −3.18 ± 0.74 [a] | −1.53 ± 1.53 [a] |
| Compound A 0.4 mg/kg BID iv (7) | −2.03 ± 1.11 [a] | −1.23 ± 0.93 [b] |
| Compound A 0.1 mg/kg BID iv (1) | −0.74 | −1.02 |

[a] $p < 0.01$,
[b] $p < 0.05$ vehicle group (ANOVA followed by a Student-Newman-Keuls test).
[d] $p < 0.001$ vs Compound A 12.5 mg/kg IV BID (ANOVA followed by a Student-Newman-Keuls test).

Conclusion:

In conclusion, experimental osteomyelitis efficacy suggest that Compound A has a therapeutic potential in the treatment of staphylococcal OM.

Example 6—Possible Formulations of Compound A (A) Formulation for Injection, 40 mg Unit Dose Composition

| Components | Unit Formula | Function |
|---|---|---|
| Drug Substance: Compound A (in the form of the bis-ethanolammonium salt) | 40.0 mg | Active substance |
| Excipients: L-Histidine, Powder | 50.0 mg | Bulking agent |
| Sterile Water for Injection | Residual Amount | Solvent |
| 0.5N Phosphoric Acid | Variable amount required for pH adjustment to 7.7 ± 0.2 | pH adjustment |
| Auxiliary Agent: Nitrogen | Not applicable | Process aid |

The product is reconstituted with 5 mL Dextrose 5% for injection and then the necessary amount of vials are diluted into a 250 or 500 mL Dextrose 5% (or 0.9% saline) infusion bag.

Oral Formulation:
Compound a 40 mg Capsules

| Component | Function | Quantity per capsules |
|---|---|---|
| Capsule fill | | |
| Compound A in the form of the bis-ethanolammonium salt | Drug Substance | 50 mg[a] |
| Capsule shell | | |
| Gelatin | Structure | 96 mg |
| Titanium Dioxide | Opacifier | 2.9% |

[a]Weight indication refers to the entire compound, i.e. the active drug moiety and the counter-ion.

Example 7—Possible Formulations of Compound B

Oral Formulation:
Compound B Tablet

| Component | Function | Quantity per tablet |
|---|---|---|
| Compound B in the form of the Tosylate monohydrate (micronized) | Drug Substance | 300.8 mg |
| Lactose monohydrate | Brittle filler | 99.9 mg |
| Microcrystalline cellulose | Ductile Filler | 70.1 mg |
| Croscarmellose Sodium | Disintegrant | 87.8 mg |
| Hydroxypropyl Cellulose | Binder | 17.6 mg |
| Poloxamer 407 | Surfactant | 5.9 mg |
| Magnesium Stearate | Lubricant | 2.9 mg |

The invention claimed is:

1. A method of treating a bacterial infection of the foot in a patient with peripheral ischemia, comprising administering to the patient an effective amount of a compound, wherein the compound is {6-[(1E)-3-{methyl[(3-methyl-1-benzofuran-2-yl)methyl]amino}-3-oxoprop-1-en-1-yl]-2-oxo-3,4-dihydro-1,8-naphthyridin-1(2H)-yl}methyl dihydrogen phosphate or a pharmaceutically acceptable salt or metabolite or pharmaceutically acceptable salt of a metabolite thereof, wherein the metabolite is (E)-N-methyl-N-((3-methylbenzofuran-2-yl)methyl)-3-(7-oxo-5,6,7,8-tetrahydro-1,8-naphthyridin-3-yl)acrylamide, and wherein the compound demonstrates dual antibacterial and vasodilatory effects.

2. The method according to claim 1, wherein the bacterial infection is caused by a Staphylococcal species including but not limited to *Staphylococcus aureus*.

3. The method according to claim 1, wherein the bacterial infection is caused by methicillin-resistant *Staphylococcus aureus*.

4. The method according to claim 1, wherein the bacterial infection is an infection of soft tissue and/or bone tissue.

5. The method according to claim 1, wherein the bacterial infection is osteomyelitis.

6. The method according to claim 1, wherein the compound is the bis-ethanolammonium salt of {6-[(1E)-3-{methyl[(3-methyl-1-benzofuran-2-yl)methyl]amino}-3-oxoprop-1-en-1-yl]-2-oxo-3,4-dihydro-1,8-naphthyridin-1(2H)-yl}methyl dihydrogen phosphate.

7. The method according to claim 1, wherein the compound is administered at a dosage of 5 mg/day to 600 mg/day.

8. The method according to claim 7, wherein the compound is administered intravenously twice daily, each administration being in a dosage of 40 mg to 160 mg.

9. The method according to claim 7, wherein the compound is administered orally twice daily, each administration being in a dosage of 40 mg to 240 mg.

10. The method according to claim 7, wherein the compound is administered intravenously three times daily, each administration being in a dosage of 40 mg to 240 mg.

11. The method according to claim 7, wherein the compound is administered orally three times daily, each administration being in a dosage of 40 mg to 240 mg.

12. The method according to claim 1, wherein the method comprises a surgical procedure to remove infected and/or necrotic tissue prior to, simultaneously with and/or after administration of said compound.

13. The method according to claim 1, wherein the method comprises administration of one or more further antibiotic agents or antibacterial agents.

14. A pharmaceutical composition, wherein the composition comprises the compound specified in claim 1.

15. The method according to claim 6, wherein the bacterial infection is caused by a Staphylococcal species including but not limited to *Staphylococcus aureus*.

16. The method according to claim 6, wherein the bacterial infection is an infection of soft tissue and/or bone tissue.

17. The method according to claim 6, wherein the bacterial infection is osteomyelitis.

18. The method according to claim 6, wherein the method comprises a surgical procedure to remove infected and/or necrotic tissue prior to, simultaneously with and/or after administration of said compound.

19. The method according to claim 6, wherein the method further comprises administration of one or more additional antibiotic agents or antibacterial agents.

20. A pharmaceutical composition, wherein the composition comprises the compound specified in claim 6.

21. The method according to claim 1, wherein the bacterial infection is a diabetic foot associated infection.

22. The method according to claim 1, wherein the compound is administered at a dosage of 40 mg/day to 720 mg/day.

23. The method according to claim 1, wherein the compound is administered at a dosage of 80 mg/day to 480 mg/day.

24. The method according to claim 1, wherein the compound is administered at a dosage of 16 mg/day to 480 mg/day.

\* \* \* \* \*